US012708383B2

(12) United States Patent
Krattiger

(10) Patent No.: US 12,708,383 B2
(45) Date of Patent: Aug. 18, 2026

(54) LITHOTRIPSY DEVICE FOR BREAKING UP CALCULI WITH A CONTROL SLEEVE, AND METHOD FOR ACCELERATING A PROJECTILE OF A LITHOTRIPSY DEVICE

(71) Applicant: KARL STORZ SE & Co. KG, Tuttlingen (DE)

(72) Inventor: Beat Krattiger, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 28 days.

(21) Appl. No.: 18/857,021

(22) PCT Filed: Apr. 3, 2023

(86) PCT No.: PCT/EP2023/058680

§ 371 (c)(1),
(2) Date: Oct. 15, 2024

(87) PCT Pub. No.: WO2023/198494

PCT Pub. Date: Oct. 19, 2023

(65) Prior Publication Data

US 2026/0191547 A1 Jul. 9, 2026

(30) Foreign Application Priority Data

Apr. 13, 2022 (DE) ..................... 10 2022 109 138.4

(51) Int. Cl.
*A61B 17/22* (2006.01)

(52) U.S. Cl.
CPC .................. *A61B 17/22012* (2013.01); *A61B 2017/22011* (2013.01); *A61B 2017/22014* (2013.01); *A61B 2017/22025* (2013.01)

(58) Field of Classification Search
CPC .... A61B 17/22012; A61B 2017/22011; A61B 2017/22014; A61B 2017/22025
See application file for complete search history.

(56) References Cited

U.S. PATENT DOCUMENTS 5,951,570 A * 9/1999 Leibersperger .. A61B 17/22012 606/128
2002/0010486 A1 1/2002 Hirt
(Continued)

FOREIGN PATENT DOCUMENTS

DE 102005022034 A1 1/2006
DE 202010001176 U1 5/2011
(Continued)

*Primary Examiner* — Brooke Labranche
(74) *Attorney, Agent, or Firm* — McGlew and Tuttle, P.C.

(57) ABSTRACT

A lithotripsy device breaks up calculi and includes a support unit, a guide tube having a cavity, a movable projectile, and proximal and distal stop elements for the projectile. The guide tube includes a proximal through-opening and a distal through-opening for feeding and/or discharging the pressure medium into and/or out of the cavity of the guide tube. A control sleeve is located in the cavity and has a cavity along a longitudinal central axis, at least one proximal opening, and at least one distal opening for the pressure medium. The projectile, with a driver element for driving the control sleeve, is located in the control sleeve cavity so that, when the control sleeve is moved along by the driver element of the projectile, a first valve-opening position and a second valve-opening position for flowing of the pressure medium are provided. A method accelerates the projectile of the lithotripsy device.

18 Claims, 4 Drawing Sheets

(56) References Cited

U.S. PATENT DOCUMENTS

| | | | | |
|---|---|---|---|---|
| 2011/0245740 | A1 | 10/2011 | Novak et al. | |
| 2020/0113777 | A1 * | 4/2020 | Novak .................. | A61H 23/04 |

FOREIGN PATENT DOCUMENTS

| | | | |
|---|---|---|---|
| DE | 202010007860 | U1 | 9/2011 |
| DE | 102020117713 | A1 | 1/2022 |
| EP | 3875045 | A1 | 9/2021 |

* cited by examiner 101
103
105
107
109
111
113
115
119
121
123
124
125
126
127
131
133
134
135
136
141
143
145
151
153
156
157
159
171
173
181
183
185
187
189
191
193
195
201
203
205
211
215
216
217
219
221
223
225

101
127
165
146
148
161
148
137
121
131
138
148
161
128
167
149
148
125
163
135
144
141
147
143
145
136
126
163
115

101
127
165
148
161
128
147
167
149
125
163
138
135
145
143
131
146
121
136
126
115
137
144
141

LITHOTRIPSY DEVICE FOR BREAKING UP CALCULI WITH A CONTROL SLEEVE, AND METHOD FOR ACCELERATING A PROJECTILE OF A LITHOTRIPSY DEVICE

CROSS REFERENCE TO RELATED APPLICATIONS

This application is a United States National Phase Application of International Application PCT/EP2023/058680, filed Apr. 3, 2023, and claims the benefit of priority under 35 U.S.C. § 119 of German Application 10 2022 109 138.4, filed Apr. 13, 2022, the entire contents of which are incorporated herein by reference.

TECHNICAL FIELD

The invention relates to a lithotripsy device for breaking up calculi, wherein the lithotripsy device comprises a support unit, a guide tube with a cavity, with a proximal end, and with a distal end, a movable projectile, and a proximal stop element and a distal stop element for the movable projectile, wherein the guide tube is at least partially arranged in the support unit, and the lithotripsy device can be assigned a drive device for supplying and/or discharging a pressure medium into an interior of the support unit and/or the guide tube, to move the projectile back and forth between the proximal stop element and the distal stop element, and a sonotrode, wherein the guide tube has at least one proximal through-opening and at least one distal through-opening for supplying and/or discharging the pressure medium into and/or out of its cavity, and the sonotrode can be connected directly or indirectly at its proximal end to the support unit and/or the guide tube and can be excited to vibration by a mechanical impact of the projectile on the distal stop element. The invention also relates to a method for accelerating a projectile of a lithotripsy device.

BACKGROUND

Lithotripsy is a well-known method for fragmenting calculi, which form as so-called concretions in body organs, for example in the bladder or kidneys, due to the condensation and/or crystallization of salts and proteins. If the calculi are too large for natural passage and cause discomfort, they must be crushed using a lithotripter so that the crushed stones can be removed by natural excretion and/or using a suction/rinsing pump. The calculi to be crushed are often inhomogeneous, with different components and/or solidities.

Pneumatic lithotripters are based on the percussion hammer principle, in which a projectile is accelerated within an acceleration tube, and the kinetic energy of the projectile is transferred via an elastic impact to the proximal end of a probe and/or sonotrode and further to its distal end to fragment the calculus. Usually, the successive impacts of the projectile are controlled by timed bursts of compressed air. As a result, the rate of the shock waves transmitted to the probe and/or sonotrode is directly dependent on the temporal sequence of the compressed air pulses applied one after the other. Consequently, the impact cadence is limited in known lithotripters due to the single-lumen acceleration tube and reversing compressed air propulsion of the projectile. In addition, a compressed air reservoir must be connected to the interior of the acceleration tube on the distal end via a connection and a switching valve in order to move the projectile back to the proximal stop after it has hit the distal end. Accordingly, the air in the connecting tube to the lithotripter must also be moved back with each pulse and escape to the outside via a resistance of a proximal switching valve, for example in the control unit. In addition to the need for pressure control, a complex operating device with a time-controlled changeover valve is required. In addition, the projectile usually does not automatically spring back at the proximal stop and thus at the reversal point, but must be accelerated again from a standstill in the distal direction using compressed air. These boundary conditions usually limit the maximum percussion cadence to well below 15 Hz.

Furthermore, known devices usually require a reversing lever to change the direction of movement of the projectile and thus to redirect the impact. Due to a loss of percussive impact caused by a reversing lever, the generation of a high distal velocity with a simultaneous high amplitude at the sonotrode and/or probe end is only possible to a limited extent.

DE 10 2020 117 713 A1 discloses a lithotripsy device having an ultrasound unit and a shock pulse unit, wherein the shock pulse unit has a guide tube with a guide channel and a constant acceleration path in which the projectile is movably mounted. The projectile is accelerated pneumatically by means of a drive device by the transmission of compressed air pulses to the guide channel, and, at the end of the acceleration path, strikes a transmission element mounted floatingly in a coupling unit, such that a shock pulse is transmitted from the projectile to the transmission element and from the transmission element further to a sonotrode head.

DE 20 2010 001 176 U1 describes a medical pressure wave device with a guide tube held in a housing in which a striking part is guided. The movement path of the striking part along the interior of the guide tube is limited by a proximal stop built into a proximal end cap- and on the opposite distal end by an impact body. The impact body is suspended in the distal end cap by means of O-rings. The striking part is driven pneumatically by means of a compressed gas supply device, which has a pneumatic compressor, which supplies a compressed gas connection of the handpiece of the pressure wave device via an external pressure line and a switching valve, which is connected to the guide tube via an opening. By opening the switching valve and applying supply pressure via the compressed gas connection to the guide tube, the striking part is accelerated in the direction of the impact body. Even before the striking part hits the impact body, the pressure is reduced again by switching the switching valve back. A return movement of the striking part immediately after impact with the impact body is facilitated by a counterpressure chamber which is connected to the distal end of the guide tube. By means of the counter pressure generated by the counterpressure chamber, the striking part is moved back to the proximal stop. For a new triggering process and thus a movement of the impactor in the distal direction, the switching valve must be switched again.

DE 20 2010 007 860 U1 relates to a pressure wave device with a pneumatic drive for generating a pressure wave, with a housing, and with a contact device for contacting a human or animal body. In this case, the contact device is mounted on the housing via a force sensor in such a way that a force transmission from the contact device to the housing takes place at least partially via the force sensor, so that a contact force can be measured by a user. The contact device is mounted in a shaft of the housing in such a way that a relative displacement between the contact device and the housing along the longitudinal axis of the housing is possible. A guide tube is held in the attachment device, wherein a relative displacement between the housing and the contact device with the guide tube proceeds under force applied by a proximal spring body. The relative displacement between the guide tube and the housing that occurs when the pressure wave device is used provides a force value via the force sensor, which substantially corresponds to the contact force. A striking part is guided in the guide tube, which can be accelerated in the distal direction by a pressure pulse of a compressed gas, wherein the movement in the distal direction is limited by an impact body elastically mounted against the contact device.

SUMMARY

It is an object of the invention to improve upon the prior art.

The object is achieved by a lithotripsy device for breaking up calculi, wherein the lithotripsy device comprises a support unit, a guide tube with a cavity, with a proximal end, and with a distal end, a movable projectile, and a proximal stop element and a distal stop element for the movable projectile, wherein the guide tube is at least partially arranged in the support unit, and the lithotripsy device can be assigned a drive device for supplying and/or discharging a pressure medium into an interior of the support unit and/or the guide tube, to move the projectile back and forth between the proximal stop element and the distal stop element, and a sonotrode, wherein the guide tube has at least one proximal through-opening and at least one distal through-opening for supplying and/or discharging the pressure medium into and/or out of its cavity, and the sonotrode can be connected directly or indirectly at its proximal end to the support unit and/or the guide tube and can be excited to vibration by a mechanical impact of the projectile on the distal stop element, wherein a control sleeve is arranged in the cavity of the guide tube, wherein the control sleeve has a cavity along its longitudinal center axis, a proximal end, a distal end, at least one proximal opening and at least one distal opening for the pressure medium, and the movable projectile is arranged in the cavity of the control sleeve with a driver element for driving the control sleeve, so that when the control sleeve is moved by means of the driver element of the projectile, a first valve-opening position exists for the pressure medium to flow through the at least one proximal through-opening of the guide tube and the at least one proximal opening of the control sleeve in and/or out of the cavity of the control sleeve for moving the projectile towards the distal stop element and a second valve-opening position exists for the pressure medium to flow through the at least one distal through-opening of the guide tube and the at least one distal opening of the control sleeve into and/or out of the cavity of the control sleeve for moving the projectile back to the proximal stop element.

As such, a lithotripsy device is provided with a self-exciting projectile with continuous supply and/or discharge of the pressure medium, in which the projectile is kept in continuous movement due to the drive provided by the control sleeve, wherein the control sleeve forms a switching valve with the guide tube, so that a constant change takes place between the first valve-opening position and the second valve-opening position for the reciprocating pressure medium drive of the projectile and thus for the back and forth movement of the projectile between the proximal stop element and the distal stop element. It is particularly advantageous that the supply and/or discharge of the pressure medium takes place continuously, so that there is no alternating pressure shock load on the components of the lithotripsy device through which the pressure medium is guided. In contrast to known pneumatic lithotripters, in which the components, such as hoses and valves, are exposed to a constant pressure load change due to the clocked pressure surges, and thus to increased wear, the continuous supply and/or discharge of the pressure medium ensures a long service life and low maintenance requirements of the lithotripsy device. In addition, the safety risk of leaks is significantly reduced. Furthermore, the more uniform movement of the pressure medium and the reduction in pressure surges reduce the tendency of the hose line to oscillate and vibrate, which allows the user to guide the instruments more comfortably and thus achieves better surgical results.

In addition, the lithotripsy device has a smaller installation space and thus a possibly reduced instrument weight, since the distal pressure reservoir with switching valve and connection to the acceleration path is omitted compared to known lithotripters.

Because the projectile, by means of the driver element, entrains the control sleeve along a determined switching path along the acceleration path until the control sleeve strikes the proximal stop element with its proximal end or the distal stop element with its distal end, then the projectile continues by itself to impact against the proximal stop element or the distal stop element, and is repulsed at the corresponding stop element and entrains the control sleeve back in the opposite direction, an automatic switching takes place for the direction of movement of the projectile and for the through-openings which are exposed for the inflow and/or outflow of the pressure medium within the lithotripsy device itself. As such, once the pressure medium supply has been started, a self-exciting process takes place in which the projectile is continuously moved back and forth by the constant pressure applied. Due to the uniform flow of pressure medium through the at least one proximal through-opening and the at least one distal through-opening of the guide tube and through the at least one proximal opening and the at least one distal opening of the control sleeve always in the same directions, and the repulsion of the projectile on the proximal stop element and the distal stop element, a higher impact cadence, in particular with a frequency of >15 Hz, preferably of >30 Hz, is achieved than with known lithotripters. Consequently, a higher impact velocity of the projectile can be achieved, which allows for better calculus removal performance than in known lithotripters. Accordingly, for the same projectile velocity, a lower pressure can be used in the lithotripsy device.

An essential idea of the invention is that of creating a valve switch for moving the projectile back and forth precisely in the interior of the lithotripsy device itself, by means of a guide tube and a control sleeve partially entrained with the projectile by means of the driver element, and only continuously supplying and/or discharging the pressure medium through the guide tube and the control sleeve. By integrating the valve switching and thus redirecting the direction of movement of the projectile, complex external supply and discharge as well as control of the pressure medium, time control of external switching valves, and a distal pressure reservoir are not required. Overall, high distal velocity with simultaneous high amplitude at the distal end of the sonotrode is achieved, thus enabling optimal and efficient calculus removal. In addition, the frequency of the mechanical impacts of the projectile on the sonotrode is not determined by external clocked pressure pulses, but rather can be specifically adjusted via the pressure medium flow, the design of the guide tube, the control sleeve, and the driver element of the projectile.

The following terminology is explained:

A "lithotripsy device" (also known as a "lithotripter") is in particular a device for fragmenting calculi using impacts, impact waves, and/or deformation waves. A lithotripsy device is understood to mean in particular various components, structural and/or functional elements of a lithotripter. The lithotripsy device can completely or partially form a lithotripter. A lithotripsy device can in particular be an intracorporeal or extracorporeal lithotripsy device. In the case of an intracorporeal lithotripsy device, this can also have a rinsing/suction pump. The lithotripsy device can be designed as a hand-held device and/or have an endoscope or be inserted into an endoscope. The lithotripsy device is in particular autoclavable and comprises, for example, instrument steel and/or plastics. The lithotripsy device can have further components, such as a control and/or supply unit, or these are assigned to the lithotripsy device. A lithotripsy device is in particular a pneumatic lithotripsy device.

"Calculi" (also known as "concretions") are understood to mean in particular all stones in a human or animal body that are formed from salts and proteins through crystallization and/or condensation. Body stones can be, for example, gallstones, urinary stones, kidney stones and/or salivary stones.

A "support unit" is in particular a hand and/or holding part of the lithotripsy device. In particular, the support unit can be a handle for manual and/or automated operation and/or connection of the lithotripsy device. The support unit can also be arranged, connected and/or automatically guided at a distal end of a robot arm. In particular, the support unit has a housing.

A "guide tube" is in particular an elongated hollow body whose length is greater than its diameter. The guide tube has in its interior in particular a cavity in which the control sleeve and a projectile that can move freely in the longitudinal direction are arranged. Furthermore, the guide tube has in particular a proximal end and a distal end, which spatially define the maximum acceleration path for the projectile. For the pneumatic drive of the projectile, the guide tube has at least one proximal through-opening and at least one distal through-opening for the passage of pressure medium into and/or out of its cavity. The guide tube constitutes, in particular, a stationary, outer valve sleeve with through-openings corresponding to the openings of the control sleeve. Instead of a tube, the guide tube can also be a hollow cylinder, with the two closed end faces directly forming the proximal and distal stop elements. The guide tube can also be connected to the proximal stop element and/or the distal stop element. For this purpose, one end of the guide tube can, for example, be arranged to engage directly in a groove in the stop element.

A "stop element" is in particular a desired end point of the movement of the projectile along the acceleration path, at which the accelerated projectile strikes the stop element, is braked, springs back and/or moves in the opposite direction. As such, the stop element absorbs the impact and/or shock of the projectile. A stop element can be, for example, a wall transverse to the longitudinal center axis of the guide tube and/or the control sleeve, a spring element, a part of an ultrasonic vibrator, such as a horn, and/or an air cushion of a compressed air spring. A proximal stop element is arranged in particular at and/or in the proximal end of the guide tube and/or within the cavity in a region of the proximal portion of the guide tube. Accordingly, a distal stop element is arranged in particular on and/or in the distal end of the guide tube and/or within the cavity in a region of the distal portion of the guide tube. The proximal stop element can, for example, be a spring element. The distal stop element is in particular directly or indirectly connected to the proximal end of the sonotrode. The distal stop element can be, for example, a spring element, a wall of a holder of the sonotrode and/or the horn aligned with the cavity of the guide tube.

"Distal end" and "distal" are understood to mean an arrangement and/or a corresponding end or portion that is close to the body and therefore remote from the user. Accordingly, "proximal end" and "proximal" are understood to mean an arrangement and a corresponding end or portion close to the user and thus remote from the body.

An "acceleration path" is in particular a portion of a longitudinal dimension of the cavity of the guide tube, which is defined by a distal stop surface of the proximal stop element and a proximal stop surface of the distal stop element. In particular, the maximum acceleration path of the projectile corresponds to the maximum longitudinal dimension of the cavity minus the projectile length when the proximal stop element is flush with the proximal end of the guide tube and the distal stop element is flush with the distal end of the guide tube. The longitudinal dimension of the cavity can, for example, be 150 mm.

A "projectile" is in particular a body which is freely movable along the acceleration path within the cavity of the guide tube. In particular, the projectile can be moved back and forth between the proximal stop element and the distal stop element within the cavity of the guide tube arranged therebetween, wherein the projectile is surrounded by the control sleeve. In principle, the projectile can have any shape. For example, the projectile may be in the shape of a bolt or a bullet. The projectile in particular has hard steel and/or magnetic properties. In order to ensure free movement, the projectile has a slightly smaller outer diameter than the diameter of the cavity of the control sleeve. For example, the projectile may have an outer diameter of 8 mm, preferably 6 mm.

The projectile can be moved back and forth in particular between the proximal stop element and the distal stop element and thus along the acceleration path continuously by means of the pressure medium of the drive device. Preferably, the projectile is continuously moved intermittently and/or oscillatingly back and forth between the proximal stop element and the distal stop element. To prevent wear of the projectile during distal and/or proximal impact, the projectile may have slightly chamfered edges at its distal end and/or proximal end.

A "driver element" is in particular an element which is arranged, fixedly or loosely connected, in and/or on an outer surface of the projectile and which, with its side opposite the projectile, rests against the inner surface of the control sleeve. The driver element is in particular designed such that, due to frictional and/or adhesive forces, it drives the control sleeve along due to the contact when a projectile moves in the control sleeve, such that the control sleeve moves along with the projectile. The driver element can, for example, be arranged in a partially or completely radially circumferential groove in the projectile. The driver element comprises in particular a polymer, such as polyoxymethylene. The driver element can, for example, be a Teflon rod or hose bent into a ring. For example, the driver element can also be made of nylon, which has low wear properties. The driver element can also be of fibrous or textile nature, e.g. felt, fleece, fabric, knitted and/or crocheted fabric. Preferably, the driver element causes only the friction and/or adhesion necessary for driving, and minimal wear. The driver element can seal the projectile and the inside of the control sleeve against each other, but the driver element does not necessarily have to be impermeable. On the contrary, a non-sealing driver element causes the pressure medium, which flows into the cavity of the control sleeve at one end of the guide tube and/or the control sleeve and thus acts on the corresponding end of the projectile, to also flow laterally past the projectile in the direction of flow to the other end of the projectile and/or guide tube and flow out through the corresponding opening in the control sleeve and through-opening of the guide tube, thereby preventing undesirable overpressures, for example in the event of a blockage.

In principle, a "drive device" can be any type of device which, by feeding and/or discharging a pressure medium, exerts a force on the projectile and thus causes the projectile to move. The drive device enables in particular a continuous and uniform inflow of the pressure medium through the proximal and distal through-openings of the guide tube and the proximal and distal openings of the control sleeve, for example pneumatically by means of compressed air, and an acceleration of the projectile within the cavity of the control sleeve and/or the guide tube.

A "pressure medium" is in particular a fluid. A pressure medium can be a gas, such as compressed air. The pressure medium can, for example, be taken from a building main line pressure supply and/or generated by a compressor. The pressure medium is in particular continuously supplied to and/or removed from the lithotripsy device and/or circulated. In particular, the pressure medium has a pressure in a range of 0 to 10 bar. Due to the continuous supply and removal of the pressure medium free from alternating loads, a pressure of >10 bar can also be used.

The "control sleeve" is in particular an elongated hollow body whose length is larger than its diameter. In particular, the control sleeve has a cavity in its interior in which the projectile can move in the longitudinal direction. The control sleeve is in particular tubular with an open proximal end and an open distal end. The control sleeve can also be designed as a hollow cylinder, with at least one opening arranged in each of the end faces. In particular, the control sleeve has a smaller diameter than the guide tube. The control sleeve has in particular at least one proximal opening and at least one distal opening for the passage of the pressure medium, wherein the proximal opening and the distal opening can each be formed on the end face and/or in the outer surface of the control sleeve. The control sleeve is arranged in the cavity of the guide sleeve in a particularly rotationally secure manner, so that the proximal through-openings of the guide tube with the proximal opening of the control sleeve and the distal through-opening of the guide tube with the proximal opening of the control sleeve can be aligned with one another in such a way that the pressure medium can flow continuously through the respective through-openings of the guide tube and the corresponding opening of the control sleeve, and thus a first valve-opening position or a second valve-opening position can be set. An anti-rotation device for the control sleeve can be implemented, for example, by a guide and/or control wire which is soldered to the control sleeve in a soldering groove in the control sleeve, exits the support unit and/or lithotripsy device through a bore in the proximal direction, and is closed off by an operating element, such as a handle. This prevents the control sleeve from rotating and allows the user to control it at the same time. In particular, the control sleeve is arranged concentrically to the guide tube. In particular, the control sleeve has a length which is shorter than the length of the guide tube. The control sleeve can have a length that is 2 mm to 30 mm, in particular 3 mm to 20 mm, preferably 4 mm to 10 mm, shorter than the length of the guide tube. The control sleeve with its proximal and distal openings is in particular axially symmetrical to its longitudinal axis and/or transverse axis.

The control sleeve and its at least one proximal opening and at least one distal opening are designed in particular such that in the event of, for example, the control sleeve striking the distal stop element, the distal through-opening of the guide tube is closed by the outer wall of the adjacent, impacted control sleeve. Likewise, when the control sleeve impacts proximally on the proximal stop element, the proximal through-opening of the guide tube is closed off by the side wall of the control sleeve. By repulsing the projectile at the respective stop element, consequently moving the projectile in the opposite direction and by driving the control sleeve by means of the driver element, the corresponding through-opening of the guide tube at the respective stop is exposed again, such that pressure medium flows through this through-opening and facilitates the further movement of the projectile in the opposite direction.

The "longitudinal center axis" is in particular the axis of the control sleeve that corresponds to the direction of its greatest extension.

A proximal and a distal "through-opening" are each a breakthrough through a wall of the guide tube. Analogously, a proximal "opening" and a distal opening are a breakthrough through a wall of the control sleeve (also called valve bores). The proximal opening and the distal opening or openings can in particular be present continuously in the outer surface of the control sleeve and/or on its two end faces—at the proximal end or distal end. As such, the open tube end of the control sleeve can form a proximal opening and/or a distal opening. The through-opening or through-openings of the guide tube as well as the distal and proximal openings of the control sleeve can each be a bore hole. In particular, these through-opening and/or openings have a relatively large diameter so that substantially no pressure loss occurs. For example, the respective through-openings of the guide tube and/or the opening of the control sleeve can have a diameter in a range of 2 to 3 mm with a guide tube diameter of 6 mm. As such, the through-openings and valve openings are designed with large cross-sections to have as little flow resistance as possible. The openings of the control sleeve may have a chamfer inside the cavity of the control sleeve in order to prevent wear and/or chip formation on the projectile.

A "sonotrode" is in particular a component that is itself set into vibration and/or resonant vibration by the action and/or introduction of mechanical vibrations. A sonotrode is, in particular, an elongated component. A sonotrode is, in particular, a probe that is, for example, rod-shaped, tubular and/or hose-shaped. The sonotrode can be an a hollow sonotrode. The sonotrode can be made in one piece or in multiple parts. In particular, the sonotrode has a diameter in the range from 0.5 mm to 4.5 mm, in particular from 0.8 mm to 3.8 mm. The sonotrode is made of steel, titanium, aluminum and/or carbon. By means of the impact energy when the projectile strikes the distal stop element, a specifically shaped deformation wave is impressed on the sonotrode in particular. In particular, the deformation wave causes a translational movement of the sonotrode, which, due to the deflection, results in improved stone fragmentation. In addition to the mechanical impact, the sonotrode can additionally be excited to vibration, in particular longitudinal vibration, in particular by means of a vibration excitation device, for example with an ultrasonic vibration exciter. In this way, the sonotrode is designed in particular as a waveguide for the vibration waves generated by a vibration excitation device and/or for the shock waves and/or deformation waves of the projectile. In particular, the proximal end of the sonotrode can rest directly or indirectly on the distal stop element. Preferably, the sonotrode is fitted on the proximal end into a threaded/retaining nipple that is thicker than its diameter. A corresponding nipple can also be a head piece. Preferably, the head piece of the sonotrode is mounted so that it can move. In particular, the sonotrode is shaped in such a way that it optimally introduces the vibration waves, deformation waves, impact waves and/or the ultrasonic vibration at its distal end into the body, the body region to be treated, and/or directly onto the calculus to be fragmented.

In a further embodiment of the lithotripsy device, the control sleeve has a second proximal opening, a third proximal opening, a fourth proximal opening and/or further proximal openings and/or a second distal opening, a third distal opening, a fourth distal opening and/or further distal openings.

As such, multiple proximal openings and/or multiple distal openings can each be distributed over the cross-section of the control sleeve and/or radially around the outer surface of the control sleeve, resulting in a more uniform flow along the cross-section by means of the pressure medium. In addition, the flow resistance can be reduced by having multiple proximal and/or distal openings.

For a corresponding design, according to the number of proximal and distal openings of the control sleeve, the guide tube has a second proximal through-opening, a third proximal through-opening, a fourth proximal through-opening and/or further proximal through-openings and/or a second distal through-opening, a third distal through-opening, a fourth distal through-opening and/or further distal through-openings.

In addition to a uniform radially circumferential arrangement of the respective proximal through-openings and/or the respective distal through-openings, the proximal through-openings and/or the distal through-openings can also be arranged at a distance in the longitudinal direction and thus along the longitudinal center axis of the control sleeve. For example, the first proximal through-opening through which the pressure medium flows into the cavity of the guide tube can be arranged closer to the proximal end of the guide tube than a second proximal through-opening through which the pressure medium flows out of the cavity of the guide tube again. This prevents a short-circuit flow and, depending on the design of the control sleeve, the first proximal through-opening with the inflowing pressure medium or the second proximal through-opening with the outflowing pressure medium can be closed off according to the movement of the projectile and the desired valve-opening position. This applies analogously to the distal through-openings.

The second, third, fourth and/or further proximal or distal openings are, in terms of their design and function, a proximal opening or distal opening as defined above. However, these additional proximal or distal openings can be arranged at a different position on the control sleeve. Likewise, the second, third, fourth and/or further proximal or distal through-openings are a proximal or distal through-opening as defined above, such that the respective through-openings can also be arranged at a different position of the guide tube. In principle, it should be emphasized that the openings and/or the through-openings can of course also have a different cross-section, but preferably these openings and/or through-openings have the same cross-section in order to ensure a uniform flow. In the guide tube, these additional proximal and/or distal through-openings are formed continuously through the outer surface.

In a further embodiment, the distal opening, the respective distal openings and/or the distal openings are arranged at the distal end and/or in an outer surface of the control sleeve and/or the proximal opening, the respective proximal opening and/or the proximal openings are arranged at the proximal end and/or in the outer surface of the control sleeve.

When the respective distal openings and/or the respective proximal openings are arranged in the outer surface, the opening runs in particular in the direction of the longitudinal center axis of the control sleeve. As a result, the respective distal and proximal openings are aligned transversely to the longitudinal center axis of the control sleeve in the longitudinal section.

In order to avoid local overpressure on the control sleeve and consequently contact of the outer surface of the control sleeve with the inner surface of the guide tube, friction between the two, and a non-uniform movement of the control sleeve, the proximal through-openings, the distal through-openings, the proximal openings and/or the distal openings are arranged axially symmetrically to the longitudinal center axis of the control sleeve.

In a further embodiment of the lithotripsy device, the guide tube has on its inner surface an at least partially radially circumferential recess or a plurality of at least partially radially circumferential recesses for guiding the pressure medium around the control sleeve.

Due to the at least partially radially circumferential recess, the pressure of the pressure medium can be distributed all around the control sleeve and consequently a local overpressure and/or undesirable friction between the outer surface of the control sleeve and the inner surface of the guide tube can be avoided.

A "recess" is in particular a cut and/or a depression in the inner surface of the guide tube. The recess can in particular be designed as an annular or partially annular groove running radially in the inner surface of the guide tube.

In order to supply and/or discharge the pressure medium to the through-openings in the guide tube in a targeted manner and to avoid different pressure losses, two or more separate chambers for passing pressure medium to and/or from the at least one proximal through-opening or the proximal through-openings and/or the at least one distal through-opening or the distal through-openings are arranged between an outer surface of the guide tube and an inner surface of the support unit.

As such, for example, a distance between the inner housing wall of the lithotripsy device and the outer surface of the guide tube can be used to divide the volume thus formed into two supply and exhaust air chambers by means of four septa or separating elements. The chambers are separated from each other, particularly in the longitudinal direction, by septa or separating elements, and run along the outside of the guide tube. For example, a rod can be arranged as a separating element between the chambers. The supply air chambers and the exhaust air chambers can be arranged alternately around the guide tube, so that two supply air chambers and two exhaust air chambers are located opposite each other.

In a further embodiment of the lithotripsy device, the distal stop element and/or the proximal stop element has/have a spring element for repulsing the projectile.

Because the projectile hits a spring element on the proximal and/or distal ends, the rebound of the projectile and thus the reversal movement is promoted. In principle, it should be emphasized that at sufficient speed the projectile is pushed back and/or moved even without a spring element on the proximal or distal stop element. However, a short dead time can occur at these reversal points, during which, at a corresponding valve-opening position, the projectile is not accelerated by the flowing pressure medium for a moment due to the switching of the through-openings for supplying the pressure medium. In order to reliably overcome this reversal point, the reversal of movement is actively initiated and accelerated by a spring element of the distal stop element and/or the proximal stop element. As a result, the corresponding through-opening of the guide tube is exposed by the control sleeve being entrained by the driver element of the moving projectile, and the projectile is further accelerated by the flow of the pressure medium through this through-opening of the guide tube and the corresponding opening of the control sleeve.

A "spring element" is in particular any element and/or component which can be sufficiently elastically deformed to overcome a short-term counterpressure at the reversal point of the reversal of movement of the projectile at the distal stop element or proximal stop element. A spring element can, for example, be a coil spring and thus a wire wound in a spiral shape with sufficient energy storage capacity. The spring element can also be arranged on the distal end and/or proximal end of the projectile. For example, the spring of the spring element can be arranged in a tube, wherein the tube preferably has the same inner diameter as the control sleeve, so that the projectile can enter the cavity of the tube of the spring element upon impact when the projectile compresses the spring. Slightly chamfered edges at the incoming end of the projectile can prevent the formation of chips at the transition into the tube of the spring element.

In order to ensure in a simple manner a repulsion of the projectile on the distal stop element and/or the proximal stop element, and thus a repeated, constant back and forth movement of the projectile along the acceleration path, the projectile and the control sleeve form a spring element, in particular a pneumatic spring, on the distal end and/or proximal side.

As a result, a spring element as an independent component cannot be destroyed by excessive speeds and/or forces upon impact of the projectile. Rather, the spring element is directly used by the projectile and the control sleeve, taking advantage of the compression space created by the accelerated approaching projectile. This is preferably an adiabatic compression of the air and/or gas space, in which essentially no energy losses occur. As such, the projectile and the control sleeve each form a pneumatic spring on the distal end and/or the proximal side, such that the control sleeve corresponds to the pressure tube and the projectile to the piston of a conventional gas pressure spring as a hydropneumatic actuating element. Consequently, the piston effect of the projectile is exploited.

In a further embodiment, the lithotripsy device has at least one connection port for connecting to the drive device and for continuously supplying or discharging the pressure medium.

As such, the drive device can be connected to the connection port of the lithotripsy device, for example with a hose.

To avoid noise during flow into or out of the lithotripter and to avoid contamination, the lithotripsy device may also have a second connection port or additional connection ports. As such, the supply air and exhaust air can be directed into and/or out of the lithotripsy device via respective connection ports. Preferably, the connection port or the connection ports are arranged on the proximal end on the outside of the lithotripsy device so that the hose connections to the drive device do not impair the handling of the lithotripsy device.

A "connection port" is any connecting element that ensures a connection between the drive device and the lithotripsy device. A connection port is in particular a short piece of pipe, such as a hose connector, a hose nozzle or a hose coupling. A connection port can also simply be an opening in the housing wall of the lithotripsy device. This opening can, for example, have an internal thread for screwing in a hose nozzle. Such an opening can also be designed without a thread and the pressure medium simply flows through this opening into the lithotripter or flows freely into the environment.

In order to provide a comprehensive and/or self-sufficient lithotripsy device, it comprises the sonotrode and/or the drive device.

In a further embodiment of the lithotripsy device, a negative pressure and/or an overpressure can be imposed on the cavity or a part of the cavity of the guide tube and/or the cavity or a part of the cavity of the control sleeve by means of the drive device.

While overpressure requires a compressor or a building pressure line with a maximum specified pressure, operating the lithotripsy device with a negative pressure and thus creating a vacuum further reduces the patient risk, simplifies the design of the corresponding control device and thus reduces costs, since complex compression, pressure control and/or pressure relief valves in the control device can be dispensed with. As such, when operating with a negative pressure, the lithotripsy device can, for example, be connected directly to an existing house vacuum in a clinic.

In a negative pressure operation, for example, to move the projectile to the distal stop element, instead of supplying compressed air via a proximal through-opening of the guide tube and a proximal opening of the control sleeve, a negative pressure is applied to a distal through-opening with the corresponding opening of the control sleeve and thus the air is sucked out of the cavity of the control sleeve, such that the projectile is moved to the distal stop element. Accordingly, the processes described in this application with regard to the inflow and feed as well as the outflow and discharge of the pressure medium apply analogously to an overpressure operation, and vice versa in the case of a negative pressure operation.

In order to achieve optimal driving of the control sleeve in the direction of movement of the projectile, the driver element has an at least partially annular friction element on and/or in a surface of the projectile and/or a medium for viscous friction.

As such, the driving of the control sleeve by means of the driver element can be based on friction, adhesion and/or viscosity. In addition to an annular design of the driver element, for example as an O-ring, it can also be partially annular and/or C-shaped, such as a clamping ring or piston ring.

For viscous friction, the driver element itself can also be formed by a medium, for example oil. As such, for example, an oil film on the outer surface of the control sleeve can be sufficient as a driver element. An adhesive or a gel can also be used as a driver element.

In a further embodiment of the lithotripsy device, the driver element has a magnetic element and the control sleeve has a counter-magnetic element.

As such, the control sleeve can be driven along via an eddy current and/or induction current, such that the driver element has at least one magnetic element or, alternatively, a magnet is built into the projectile or the projectile itself is designed as a permanent magnet. The movement creates eddy currents and/or induction currents in the control sleeve and carries the control sleeve along with the projectile.

In order to start or stop the lithotripsy device and to trigger an individual movement of the projectile, the lithotripsy device and/or the support unit has an operating unit for starting, stopping and/or individually triggering a movement of the projectile.

As such, the movement of the control sleeve and/or the projectile can be controlled from the outside by an operator using a control mechanism on the control unit. Preferably, the control unit and/or individual operating elements are ergonomically arranged on the outside of the support unit and/or the housing of the lithotripsy device. By operating the switching function on the lithotripsy device itself, the otherwise usual foot switch for triggering a shock wave of the projectile can be dispensed with, thus reducing the costs of the lithotripsy device and improving clarity in the operating room.

In a further embodiment, the lithotripsy device has a counter bearing and a horn, and at least one piezo element is arranged as a vibration exciter and mechanically coupled between the counter bearing and the horn, wherein the horn has the distal stop element and/or the horn is connectable to the distal stop element and/or the sonotrode and the at least one piezo element is electrically connectable to an assignable ultrasound generator, so that a combined vibration excitation of the sonotrode can be realized by means of the drive device and the at least one piezo element.

Consequently, the sonotrode can be simultaneously excited by both a constant vibration excitation and a repetitive impact excitation, by imposing deformation waves. This achieves further increased efficiency in the comminution of calculi by means of a dual fragmentation and/or action mechanism. It is particularly advantageous that a substantially constant ultrasonic energy can be supplied to the sonotrode by means of the vibration exciter, for example an ultrasonic generator, and the at least one piezo element, while a repeating, intermittent, but very uniform ballistic deformation wave energy can be transferred to the sonotrode by means of the drive device, such that the latter can above all impart a high distal velocity with a simultaneously high amplitude with a frequency of >13 Hz.

A "horn" is in particular a component that is arranged between the vibration exciter and sonotrode. The horn is used in particular to forward and/or orient the ultrasonic waves generated by the vibration exciter to the sonotrode. The horn can also be used to fasten the sonotrode. At the same time, the horn serves to mechanically hold the vibration exciter on both sides, in particular together with a counter bearing.

A "vibration exciter" is in particular a component of an ultrasonic transducer and/or lithotripsy device which converts a supplied alternating voltage with a specific frequency into a mechanical vibration frequency. The vibration exciter is in particular an electromechanical transducer utilizing the piezoelectric effect. Due to the application of an alternating electrical voltage generated by an ultrasonic generator, a mechanical vibration is generated as a result of deformation of the vibration exciter. In particular, the vibration exciter has one or more piezo elements. Preferably, the vibration exciter has at least two piezo elements, wherein an electrical conductor, for example a copper disk, can be arranged between the piezo elements. In the case of ultrasonic excitation, the sonotrode operates in particular in the ultrasonic range with a frequency range from 20 kHz to 90 kHz, preferably from 20 kHz to 34 kHz.

In a further aspect of the invention, the object is achieved by a method for accelerating a projectile of a lithotripsy device, wherein the lithotripsy device has a guide tube with a cavity and a control sleeve in the cavity of the guide tube, wherein the projectile movable between a proximal stop element and a distal stop element is arranged in a cavity of the control sleeve, and the movable projectile has a driver element for driving the control sleeve, the lithotripsy device can be assigned a drive device for supplying and/or discharging a pressure medium, the guide tube has at least one proximal through-opening and at least one distal through-opening for supplying and/or discharging the pressure medium into and/or out of its cavity, and the control sleeve has at least one proximal opening and at least one distal opening for the pressure medium, with the following steps:

supplying and/or discharging the pressure medium into the cavity of the guide tube by means of the drive device, flowing the pressure medium through the at least one proximal through-opening of the guide tube and the at least one proximal opening of the control sleeve into the cavity of the control sleeve and moving the projectile towards the distal stop element, and entraining the control sleeve along by means of the driver element of the projectile, and/or repulsing the projectile on the distal stop element, and/or flowing the pressure medium through the at least one distal through-opening of the guide tube and the at least one distal opening of the control sleeve into the cavity of the control sleeve and moving the projectile back to the proximal stop element, and entraining the control sleeve by means of the driver element of the projectile, and/or repulsing the projectile on the proximal stop element.

As such, by means of the method, the user can very easily and quickly realize a repeated back and forth movement of the projectile along the acceleration path after starting the lithotripsy device by the self-exciting projectile with the switching control sleeve, without having to pay attention to pressures and valve switching of an external pressure medium supply. The method described above refers to an overpressure operation; in a negative pressure operation, a suction pressure is applied to the distal through-opening of the guide tube and thus to the corresponding distal opening of the control sleeve in order to move the projectile towards the distal stop element. Accordingly, when the projectile moves back to the proximal stop element, the suction pressure is applied to the proximal through-opening of the guide tube and the distal opening of the control sleeve.

In a further embodiment of the method, the supply and/or discharge of the pressure medium is carried out continuously.

This allows the user to continuously use a self-controlled method to accelerate a projectile without having to constantly pay attention to the timing of the pressure pulse, as is the case with conventional pneumatic lithotripters.

The invention is explained in more detail below with reference to exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
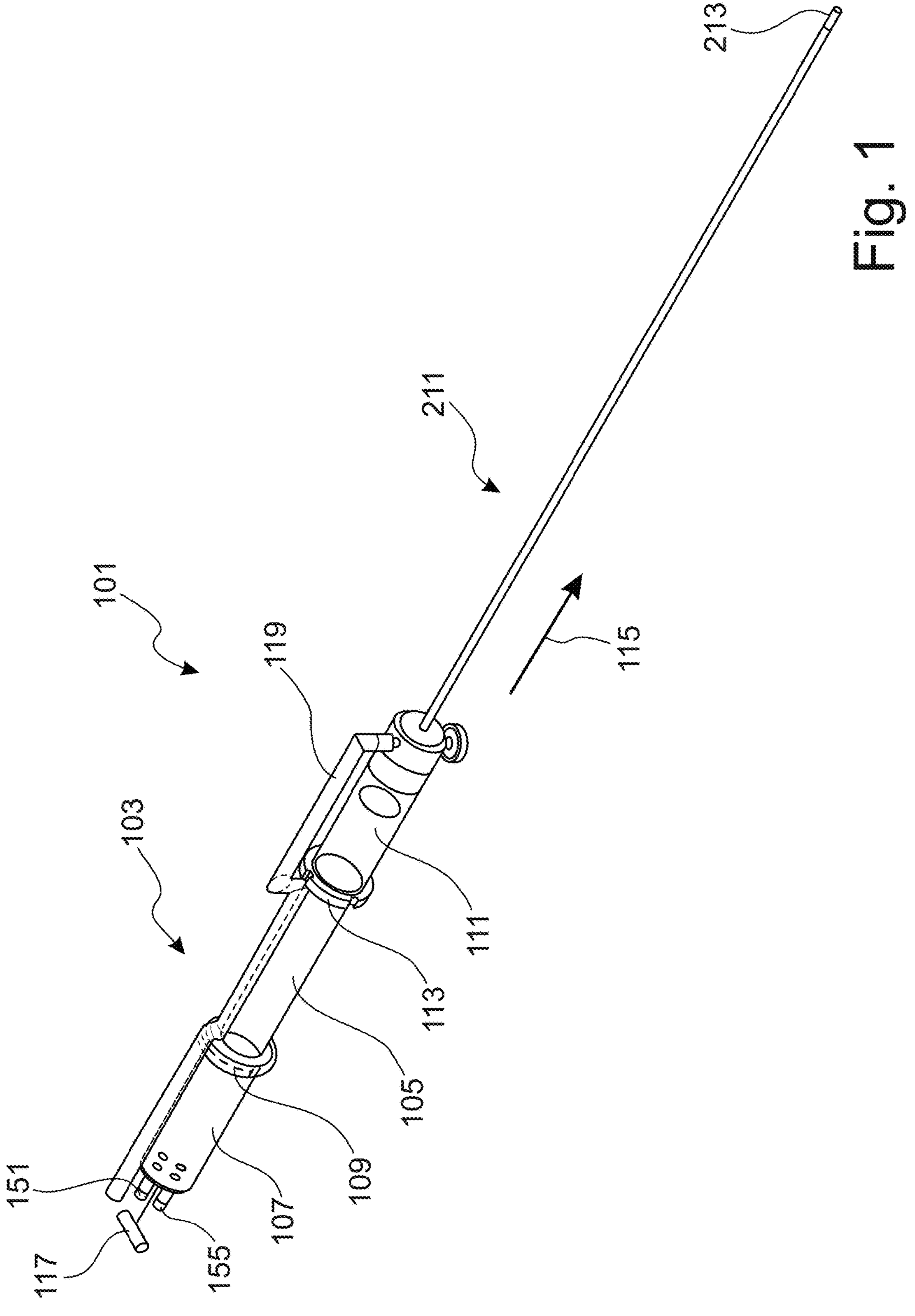
FIG. 1 is a highly schematic three-dimensional representation of a lithotripsy device.

Referring to the drawings, a lithotripsy device 101 has a support unit 103 with a central housing tube 105. At a proximal end of the housing tube 105, a proximal end cap 107 is screwed onto the housing tube 105 by means of a proximal lock nut 109. Likewise, a distal end cap 111 is screwed onto the distal end of the housing tube 105 by means of a distal lock nut 113 (see FIG. 1 and FIG. 2). At the proximal end of the proximal end cap 107, a first exhaust air connection 151 and a second exhaust air connection 153, not visible in FIG. 1, are arranged. Furthermore, a first supply air connection 155 and a second supply air connection 156, not visible in FIG. 1, are arranged on the proximal end of the proximal end cap 107. From the distal end portion of the distal end cap 111, a suction line 119 for suctioning calculus fragments is guided against a distal direction 115 to the proximal end of the lithotripsy device 101. The suction line 119 is shown only symbolically in FIG. 1 and has impractically tight bending radii. Likewise, in FIG. 1, an operating element 117 at the proximal end of the support unit 103 is shown only symbolically, wherein the operating element 117 is arranged in an optimally ergonomic manner on the housing tube 105 in an alternative embodiment. The operating element 117 is designed with a control sleeve 131 arranged inside the housing tube 105 for starting and switching off, as well as for single and/or continuous firing by means of the ballistic lithotripsy device 101. At the distal end of the support unit 103, an elongated sonotrode 211 designed as a hollow probe with a sonotrode tip 213 is arranged.

Figure 2:
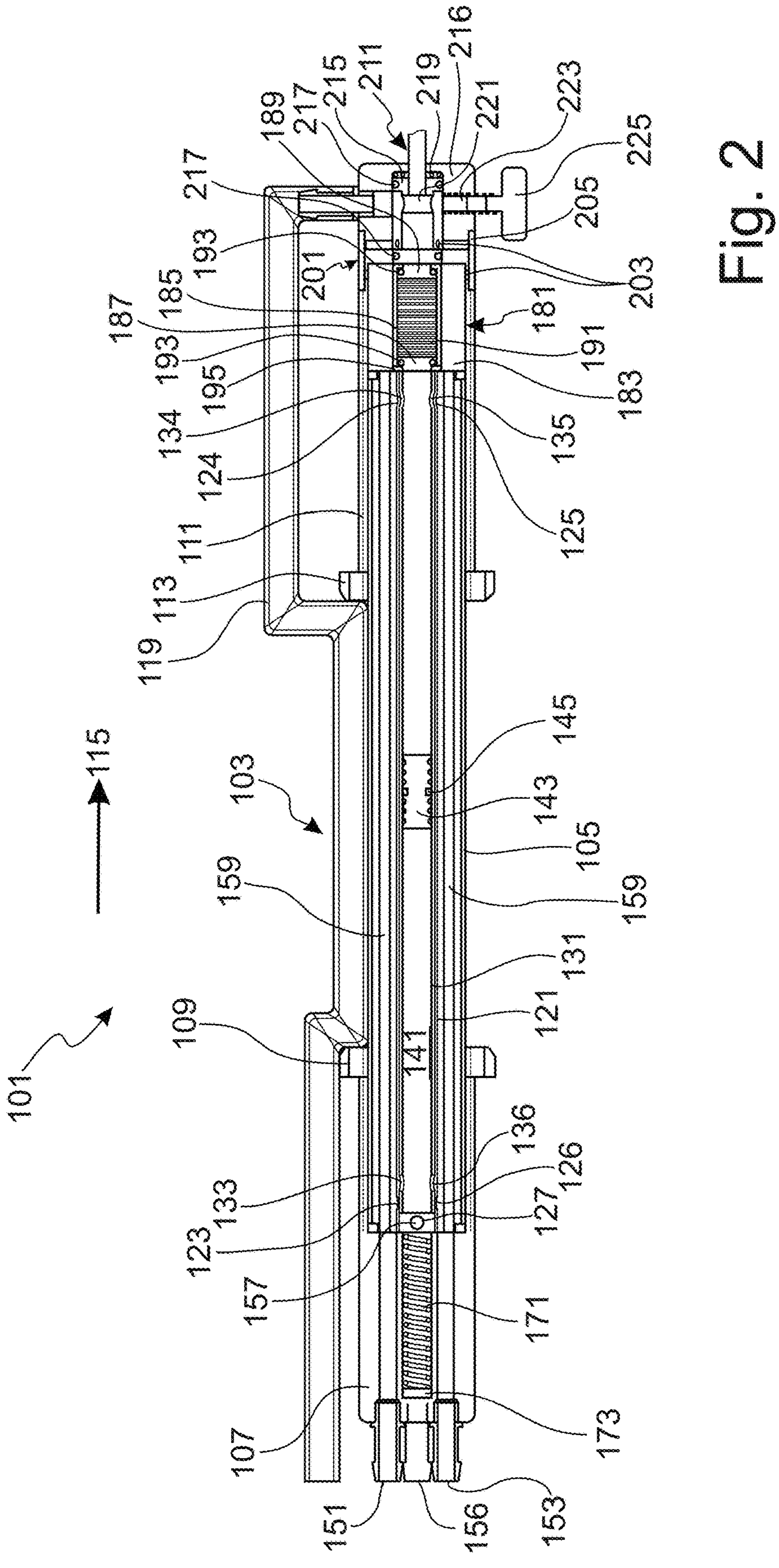
FIG. 2 is a schematic representation of the lithotripsy device with a guide tube and a control sleeve in longitudinal section during a movement of a projectile in the distal direction.

Inside the housing tube 105 of the support unit 103, a guide tube 121 is arranged at a distance from the housing tube 105, wherein between an inner wall of the housing tube 105 and an outer wall of the guide tube 121, two supply air chambers 157 and exhaust air chambers 159 are arranged symmetrically on the cross section, which are connected via bore holes in the proximal end cap 107 to the crosswise-arranged first exhaust air connection 151 and the second exhaust air connection 153, as well as the first supply air connection 155 and the second supply air connection 156 (in FIG. 2, one supply air chamber 157 is located behind a fifth through-bore 127 and is only visible through this, while the second supply air chamber is located in front of the viewing plane). The supply air chambers 157 and the exhaust air chambers 159 extend over the entire length of the guide tube 121. The two exhaust air connections 151, 153 and the two supply air connections 155, 156 are each connected via a Y-connector (not shown) to an exhaust air hose and a supply air hose of a drive device (not shown).

The guide tube 121 has on the proximal end a first through-bore 123 and a fourth through-bore 126, which are each connected to one of the two exhaust air chambers 159. On the distal end, the guide tube 121 has a second through-bore 124 and a third through-bore 125, which are each connected to one of the two exhaust air chambers 159. Furthermore, the guide tube 121 has a fifth through-bore 127 on the proximal end and a further through-bore opposite, and therefore not visible in FIG. 2, which are each connected to one of the two supply air chambers 157 (the two corresponding distal through-bores connected to the supply air chambers 157 are not shown in FIG. 2). All through-bores 123, 124, 125, 126, 127 pass transversely through the outer surface of the guide tube 121 and each have a diameter of 3 mm.

The control sleeve 131 is arranged inside the guide tube 121 and has a first valve bore 133 and a fourth valve bore 136 on the proximal end corresponding to the proximal through-bores 123, 126 of the guide tube 121. Accordingly, a second valve bore 134 and a third valve bore 135 are provided in the control sleeve 131 on the distal end. The control sleeve 131 is arranged in a rotationally secure manner within the guide tube 121, so that the corresponding through-bores of the guide tube 121 and the valve bores of the control sleeve 131 are fully open in their respective valve-opening positions. The control sleeve 131 has a cavity 141 on the inside, which simultaneously forms an acceleration path for a projectile 143. The projectile 143 has on its outer surface a driver ring 145 which rests externally on an inner surface of the control sleeve 131. The control sleeve 131 is 4 mm shorter than the guide tube 121.

On the proximal side of the control sleeve 131, a return spring 171 is arranged in a sheath tube, which is held in the proximal end cap 107 by means of a holder 173.

At the distal end of the control sleeve 131, a tempering spring 181 is arranged for imparting a defined deformation wave to the sonotrode 211 due to the mechanical impact of the projectile 143. The tempering spring 181 has a plurality of stacked polymer disks 191 in the distal direction 115, which are surrounded on the outside by a sheath tube 185. The sheath tube 185 is held in the distal end cap 111 by means of a holder 183. At the proximal end of the sheath tube 185, a proximal end cap 187 is arranged, which has an O-ring 193 on the inside and is captive, in a manner allowing movement, held by means of a welding ring 195, which is welded to the sheath tube 185. On the distal end, a distal end cap 189 is arranged, which is also captive, in a manner allowing movement, held by means of a flange of the sheath tube 185. It also has an O-ring 193 on the inside.

As such, the distal end of the return spring 171 constitutes a proximal stop element and the proximal end cap 187 of the tempering spring 181 constitutes a distal stop element for the projectile 143. FIG. 2 shows the state in which the control sleeve 131 is struck in a distal direction 115 against the distal stop element formed by the proximal end cap 187 of the tempering spring 181. Since the control sleeve 131 is 4 mm shorter than the guide tube 121, the cavity of the guide tube 121 in the region of the proximal fifth through-opening 127 is free of the control sleeve 131. After repulsation of the projectile 143 at the end cap 187 of the tempering spring 181, the projectile 143 moves back against the distal direction 115 and entrains the control sleeve 131 by means of the driver ring 145. As a result of this return movement, the opposite distal through-openings of the guide tube 121 (not shown in FIG. 2) and the associated valve openings for the entry of supply air into the cavity 141 of the control sleeve 131 become freely passable, and the incoming supply air pushes the projectile 143 further in the proximal direction. Due to this backward movement of the projectile 143 and the entrainment of the control sleeve 131, the first valve bore 133 of the control sleeve 131 is pushed to the first through-bore 123 of the guide tube 121 and the fourth valve bore 136 of the control sleeve 131 is pushed to the fourth through-bore 126 of the guide tube 121 over a distance of 4 mm, with a defined stop of the proximal end of the control sleeve 131 against the distal end wall of the sheath tube of the return spring 171, such that the respective through-bore and valve bore are aligned for the exit of exhaust air into the exhaust air chambers 159. At the same time, the fifth through-bore 127 and the other, invisible through-bore opposite are closed off to block the passage of supply air. After repulsion of the projectile 143 at the proximal stop by means of the return spring 171 and followed by renewed movement in the distal direction 115, the control sleeve 131 is again entrained by the projectile 143 by means of the driver ring 145, and accordingly the fifth through-bore 127 and the opposite, invisible further through-bore are opened. Through this, supply air enters the cavity 141 of the control sleeve 131 and moves the projectile 143 further in the distal direction 115 until the state shown in FIG. 2 is reached again.

A head piece 215 of the sonotrode 211 is arranged distally of the tempering spring 181, wherein the head piece 215 is movably mounted in a guide part 216 at its proximal end and its distal end by means of O-rings 217. The head piece 215 has a transverse bore 221 in which a plunger 223 loosely engages with an operating handle 225 as an anti-rotation device, and for removing calculus fragments. The plunger 223 is held in position by a spring not shown in FIG. 2. By pressing the plunger 223 into the transverse bore 221 by means of the operating handle 225, fragments of calculi can be removed from the head piece 215. A damping element 219 for limiting an amplitude of the sonotrode 211 is arranged on the distal end of the head piece 215.

Relief bores 203 to the head piece 215 of the sonotrode 211 and to the holder 183 of the tempering spring 181 are provided in the distal end cap 111, which together with a respective elastomer ring 205 form a pressure relief valve 201 to the holder 183 of the tempering spring 181 and to the head piece 215 of the sonotrode 211 in order to prevent the action of excess pressure in the patient during use of the lithotripsy device 101, in the event of a malfunction occurring.

Figure 3:
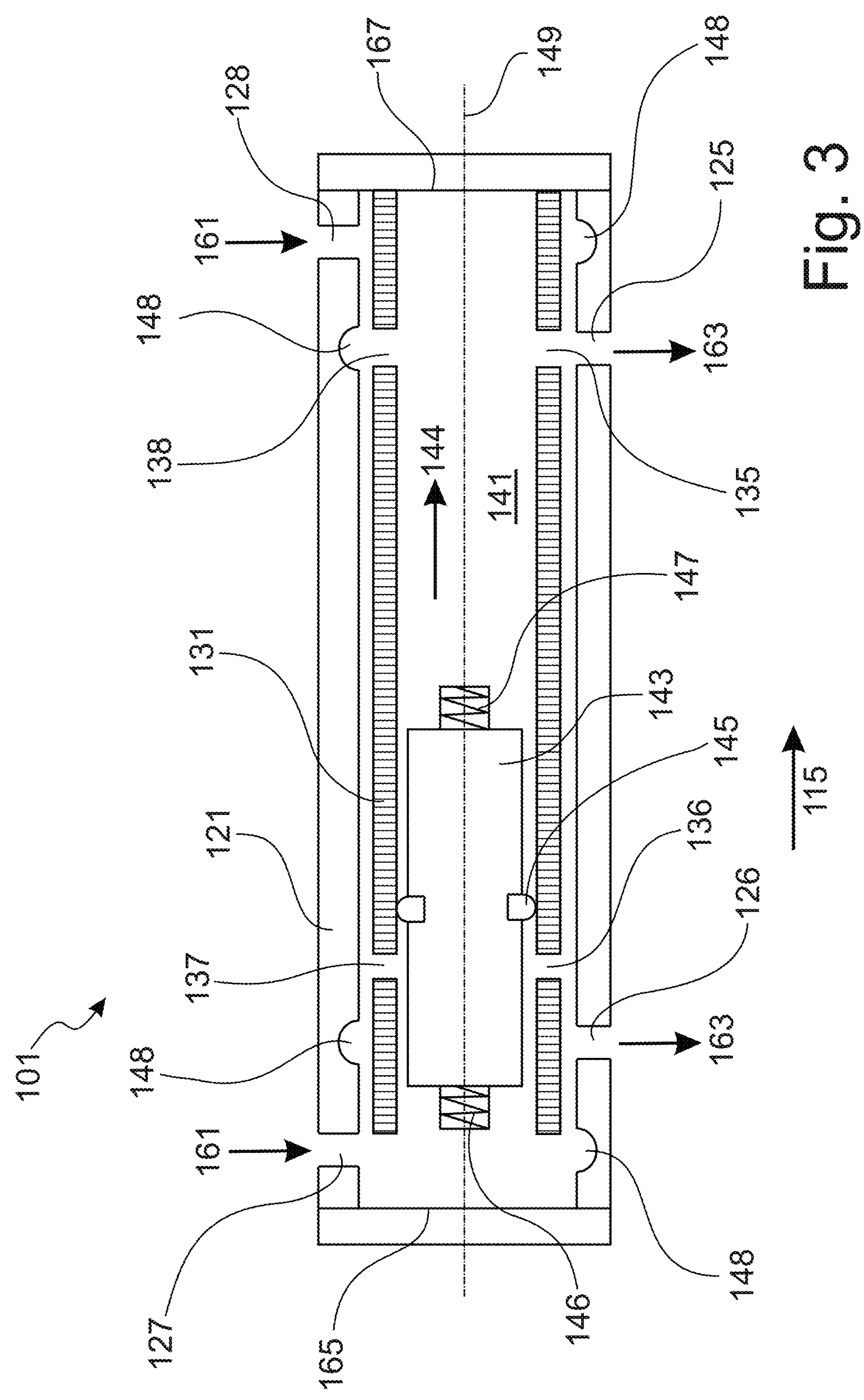
FIG. 3 is a highly schematic representation of the functional principle of a guide tube and a control sleeve of a lithotripsy device during a movement of a projectile in the distal direction.
Figure 4:
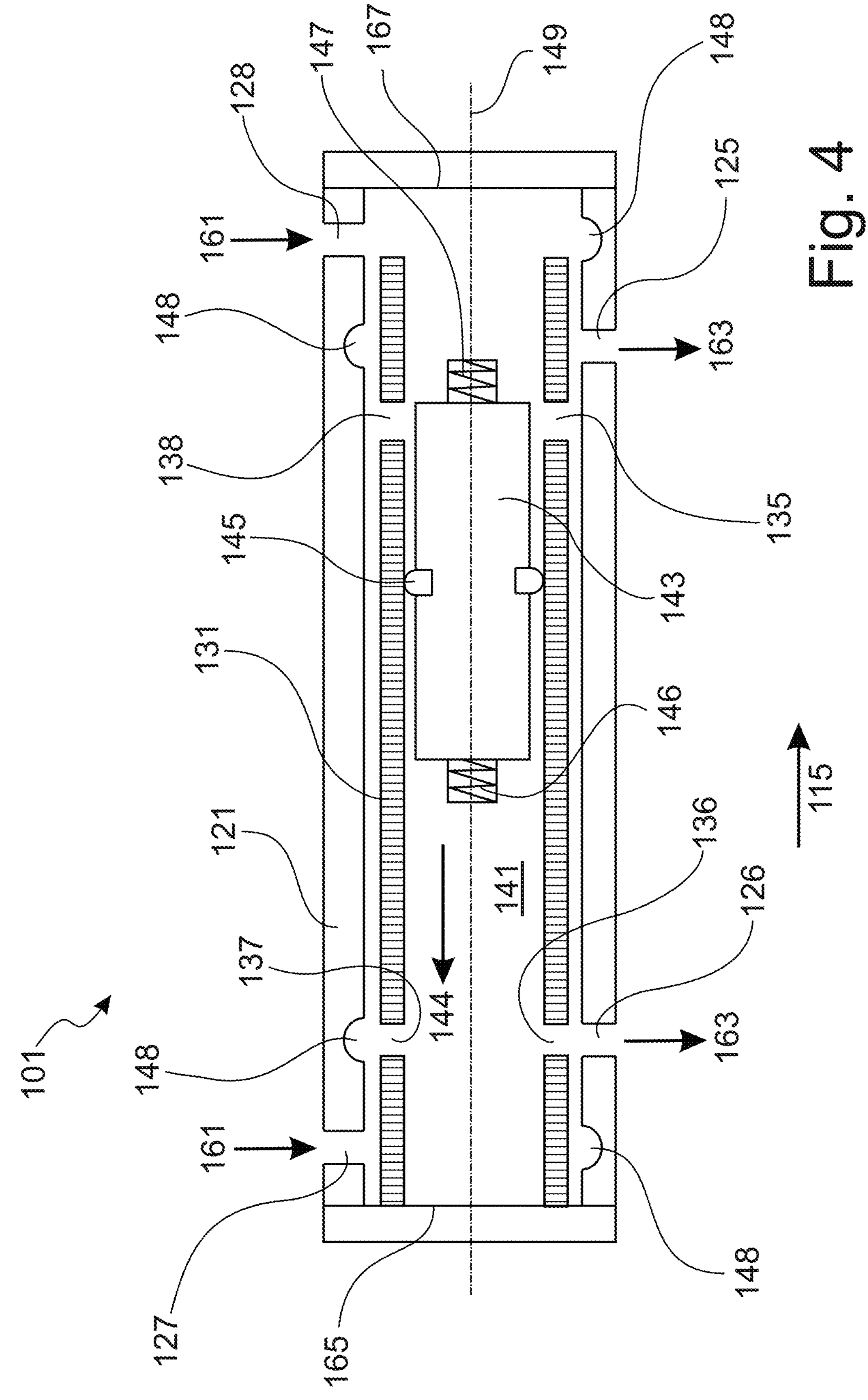
FIG. 4 is a highly schematic representation of the functional principle of the guide tube and the control sleeve from FIG. 3 during a movement of the projectile in the proximal direction.

To explain the functional principle and the drive, the lithotripsy device 101 with the guide tube 121 and the internal control sleeve 131 is shown in a highly simplified manner in FIGS. 3 and 4, in which only one through-opening for supply air and exhaust air is shown on the distal end and proximal end; for reasons of illustration, these are also shown in the same plane. The guide tube 121 has on the proximal end a fifth through-bore 127 for supply air and a fourth through-bore 126 for exhaust air, which pass through an outer surface of the guide tube 121 and are slightly offset along a longitudinal center axis 149 of the guide tube 121 and the control sleeve 131, which are arranged concentrically to one another. On the distal end, the guide tube 121 has a sixth through-bore 128 for supply air and a third through-bore 125 for exhaust air, which are also arranged offset along the longitudinal center axis 149. Opposite the fifth through-bore 127, the sixth through-bore 128, the third through-bore 125 and the fourth through-bore 126, a recess 148 is formed as a radially circumferential groove in the inner surface of the guide tube 121, wherein the radially circumferential groove has a greater width than a diameter of the respective through-bore 125, 126, 127, 128.

The control sleeve 131 arranged in the cavity of the guide tube 121 has a fifth valve bore 137 on the proximal end and a fourth valve bore 136 opposite. On the distal end, the control sleeve 131 has a sixth valve bore 138 and an opposite third valve bore 135. In the cavity 141, a projectile 143 is arranged, which has on its outer surface a driver ring 145 which is in external contact with the inner surface of the control sleeve 131. The projectile 143 is movable within the cavity 141 along an acceleration path between a proximal stop element 165 and a distal stop element 167. The projectile 143 has at its proximal end a proximal spring element 146 for repulsion at the proximal stop element 165 and at its distal end a distal spring element 147 for repulsion at the distal stop element 167. Alternatively, the two spring elements 146, 147 are each arranged on the proximal stop element 165 and the distal stop element 167 (as described above for FIG. 2).

The lithotripsy device 101 is started by means of an operating element, and compressed air is continuously supplied by a drive device (not shown in FIGS. 3 and 4) in an air supply direction 161 through the fifth through-bore 127 and/or the sixth through-bore 128 of the guide tube 121. Likewise, the compressed air from the cavity 141 continuously leaves the guide tube 121 in an exhaust direction 163 through the third through-bore 125 and/or the fourth through-bore 126.

FIG. 3 shows a state in which the driven control sleeve 131 is struck with its distal end against the distal stop element 167 in the distal direction 115 during a movement of the projectile 143, due to the entrainment by the driver ring 145 in a projectile movement direction 144. As a result, the sixth through-bore 128 of the guide tube 121 is blocked by the control sleeve 131, while the offset, opposite third through-bore 125 of the guide tube 121 is opened, so that compressed air is forced out of the third through-bore 125 as exhaust air in the distal direction 115 due to the projectile movement direction 144. At the proximal end of the tubular control sleeve 131, the fifth through-bore 127 of the guide tube 121 is exposed, so that compressed air as supply air presses through this fifth through-bore 127 and the exposed proximal tube opening of the control sleeve 131, directly onto the proximal end of the projectile 143, and moves it further in the projectile movement direction 144 until it strikes the distal stop 167. Accordingly, the fourth through-bore 126, which is offset opposite the fifth through-bore 127, is closed off by the control sleeve 131 attached to the distal stop element 167, so that the incoming compressed air is only used to move the projectile 143 in the direction of movement 144, and cannot flow out (see FIG. 3).

After the projectile 143 has struck the distal stop element 167, it is repulsed by the distal spring element 147 and moved in the opposite direction to the distal direction 115. In this case, the projectile 143 entrains the control sleeve 131 in the proximal direction due to the driver ring 145 until the control sleeve 131 is struck with its proximal end against the proximal stop element 165 (see state as shown in FIG. 4). The projectile 143 then continues to move alone in the projectile movement direction 144 opposite to the distal direction 115. Due to the impact of the control sleeve 131 on the proximal stop element 165, the sixth through-bore 128 at the distal end of the guide tube 121 is then exposed, and the compressed air flows continuously through this sixth through-bore 128 and directly through the distal tube opening of the control sleeve 131 against the distal end of the projectile 143, such that the latter is moved further in the projectile movement direction 144 against the proximal stop element 165. In order to effectively produce this movement, the third through-bore 125 of the guide tube 121 at the distal end portion of the guide tube 121 is closed off by the control sleeve 131 attached on the proximal end. Likewise, the fifth through-bore 127 for supplying the compressed air through the attached control sleeve 131 is closed on the proximal end, while the offset opposite fourth through-bore 126 is open for discharging the compressed air compressed by the movement of the projectile 143 in the projectile movement direction 144. The compressed air is optimally and evenly distributed radially around the control sleeve 131 by means of the grooves machined all the way around the inner surface of the guide tube 121 at the position of the through-bores 125, 126, 127 and 128, which are visible in FIGS. 3 and 4 as oppositely arranged recesses 148. This prevents local lateral overpressure and friction and/or jamming of the control sleeve 131 on the guide tube 121 when the control sleeve 131 is moved by the projectile 143 by means of the driver ring 145. Furthermore, due to the circumferential grooves, an anti-rotation device for the control sleeve 131 can be dispensed with in this case.

As already described above for the distal stop element 167, the projectile 143 is repulsed when it strikes the proximal stop element 165, due to the proximal spring element 146, and is accordingly moved again in the distal direction 115. During this reversal of movement, the control sleeve 131 is again moved in the distal direction 115, and the processes described above are repeated.

As such, a lithotripsy device 101 is provided in which an automatic valve changeover for moving a self-exciting projectile back and forth along an acceleration path is realized internally by the design of the guide tube 121, the control sleeve 131 and the projectile 143, wherein the process is automatically repeated in a synchronized manner with a continuous flow through the guide tube 121 and the control sleeve 131 itself. This eliminates the need for complex a control loop, and valve switching of an external, intermittent compressed air supply.

While specific embodiments of the invention have been shown and described in detail to illustrate the application of the principles of the invention, it will be understood that the invention may be embodied otherwise without departing from such principles.

LIST OF REFERENCE NUMBERS

101 Lithotripsy device
103 Support unit
105 Housing tube
107 Proximal end cap
109 Proximal lock nut
111 Distal end cap
113 Distal lock nut
115 Distal direction
117 Operating element
119 Suction line
121 Guide tube
123 First through-bore for exhaust air
124 Second through-bore for exhaust air
125 Third through-bore for exhaust air
126 Fourth through-bore for exhaust air
127 Fifth through-bore for supply air
128 Sixth through-bore for supply air
131 Control sleeve
133 First valve bore
134 Second valve bore
135 Third valve bore
136 Fourth valve bore
137 Fifth valve bore
138 Sixth valve bore
141 Cavity/Acceleration path
143 Projectile
144 Projectile movement direction
145 Driver ring
146 Proximal spring element
147 Distal spring element
148 Recess
149 Longitudinal center axis
151 First exhaust air connection
153 Second exhaust air connection
155 First supply air connection
156 Second supply air connection
157 Supply air chamber
159 Exhaust chamber
161 Supply air direction
163 Exhaust air direction
165 Proximal stop element
167 Distal stop element
171 Return spring
173 Holder
181 Tempering spring
183 Holder
185 Sheath tube
187 Proximal end cap
189 Distal end cap
191 Polymer disks
193 O-ring
195 Welding ring
201 Pressure relief valve
203 Ventilation bore
205 Elastomer ring
211 Sonotrode
213 Sonotrode tip
215 Head piece
216 Guide part
217 O-ring
219 Damping element
221 Transverse bore
223 Plunger
225 Operating handle

The invention claimed is:

1. A lithotripsy device for breaking up calculi, wherein the lithotripsy device comprises:

a support unit, a guide tube with a cavity, with a proximal end, and with a distal end, a movable projectile, a proximal stop element, a distal stop element for the movable projectile, wherein the guide tube is arranged at least partially in the support unit, and the lithotripsy device is configured to be assigned a drive device for supplying and/or discharging a pressure medium into an interior of the support unit and/or the guide tube, to move the projectile back and forth between the proximal stop element and the distal stop element, and a sonotrode, wherein the guide tube has at least one proximal through-opening and at least one distal through-opening for supplying and/or discharging the pressure medium into and/or out of the guide tube cavity, and the sonotrode can be connected directly or indirectly at its proximal end to the support unit and/or the guide tube and can be excited to vibrate by a mechanical impact of the projectile on the distal stop element, and a control sleeve is arranged in the cavity of the guide tube, wherein the control sleeve has a cavity along a control sleeve longitudinal center axis, a proximal end, a distal end, at least one proximal opening and at least one distal opening for the pressure medium, and in the cavity of the control sleeve the movable projectile is arranged with a driver element for driving the control sleeve, so that when the control sleeve is moved by means of the driver element of the projectile, a first valve-opening position exists for the flow of the pressure medium through the at least one proximal through-opening of the guide tube and the at least one proximal opening of the control sleeve into and/or out of the cavity of the control sleeve, to move the projectile towards the distal stop element, and a second valve-opening position exists for the flow of the pressure medium through the at least one distal through-opening of the guide tube and the at least one distal opening of the control sleeve into and/or out of the cavity of the control sleeve, to move the projectile back to the proximal stop element.

2. The lithotripsy device according to claim 1, wherein the control sleeve has a second proximal opening, a third proximal opening, a fourth proximal opening and/or further proximal openings and/or a second distal opening, a third distal opening, a fourth distal opening and/or further distal openings.

3. The lithotripsy device according to claim 2, wherein the proximal through-openings, the distal through-openings, the proximal openings and/or the distal openings are arranged axially symmetrically to the longitudinal center axis of the control sleeve.

4. The lithotripsy device according to claim 1, wherein the guide tube has a second proximal through-opening, a third proximal through-opening, a fourth proximal through-opening and/or further proximal through-openings and/or a second distal through-opening, a third distal through-opening, a fourth distal through-opening and/or further distal through-openings.

5. The lithotripsy device according to claim 1, wherein the distal opening, the given distal opening, and/or the distal openings is or are arranged at the distal end and/or in an outer surface of the control sleeve, and/or the proximal opening, the given proximal opening, and/or the proximal openings is or are arranged at the proximal end and/or in the outer surface of the control sleeve.

6. The lithotripsy device according to claim 1, wherein the guide tube has in a guide tube inner surface an at least partially radially circumferential recess or a plurality of at least partially radially circumferential recesses for guiding the pressure medium around the control sleeve.

7. The lithotripsy device according to claim 1, wherein two or more separate chambers for passing pressure medium to and/or from the at least one proximal through-opening or the proximal through-openings and/or the at least one distal through-opening or the distal through-openings are arranged between an outer surface of the guide tube and an inner surface of the support unit.

8. The lithotripsy device according to claim 1, wherein the distal stop element and/or the proximal stop element has/have a spring element for repulsing the projectile.

9. The lithotripsy device according to claim 1, wherein the projectile and the control sleeve form a spring element, comprising a pneumatic spring, on the distal end and/or the proximal end.

10. The lithotripsy device according to claim 1, wherein the lithotripsy device has at least one connection port for connecting to the drive device and for continuously supplying or discharging the pressure medium.

11. The lithotripsy device according to claim 1, wherein the lithotripsy device further comprises the sonotrode and/or the drive device.

12. The lithotripsy device according to claim 11, wherein, by means of the drive device, a negative pressure and/or an overpressure can be impressed on the cavity or a part of the cavity of the guide tube and/or the cavity or a part of the cavity of the control sleeve.

13. The lithotripsy device according to claim 1, wherein the driver element has an at least partially annular friction element on and/or in a surface of the projectile and/or a medium for viscous friction.

14. The lithotripsy device according to claim 1, wherein the driver element has a magnetic element and the control sleeve has a counter-magnetic element.

15. The lithotripsy device according to claim 1, wherein the lithotripsy device and/or the support unit comprises an operating unit for starting, stopping and/or individually triggering a movement of the projectile.

16. The lithotripsy device according to claim 1, further comprising a counter bearing and a horn, and at least one piezo element arranged and mechanically coupled between the counter bearing and the horn as a vibration exciter, wherein the horn has the distal stop element and/or the horn can be connected to the distal stop element and/or the sonotrode, and the at least one piezo element is configured to be electrically connected to an assignable ultrasound generator, so that a combined vibration excitation of the sonotrode can be realized by means of the drive device and the at least one piezo element.

17. A method for accelerating a projectile of a lithotripsy device, wherein the lithotripsy device has a guide tube with a cavity and a control sleeve in the cavity of the guide tube, wherein the projectile, movable between a proximal stop element and a distal stop element, is arranged in a cavity of the control sleeve, and the movable projectile has a driver element for driving the control sleeve, the lithotripsy device is configured to be assigned a drive device for supplying and/or discharging a pressure medium, the guide tube has at least one proximal through-opening and at least one distal through-opening for supplying and/or discharging the pressure medium into and/or out of its cavity, and the control sleeve has at least one proximal opening and at least one distal opening for the pressure medium, the method comprising the following steps:

supplying and/or discharging the pressure medium into the cavity of the guide tube by means of the drive device, flowing the pressure medium through the at least one proximal through-opening of the guide tube and the at least one proximal opening of the control sleeve into the cavity of the control sleeve and moving the projectile towards the distal stop element, and moving the control sleeve by means of the driver element of the projectile, and/or repulsing the projectile on the distal stop element, and/or flowing the pressure medium through the at least one distal through-opening (128) of the guide tube and the at least one distal opening of the control sleeve into the cavity of the control sleeve and moving the projectile back to the proximal stop element, and moving the control sleeve by means of the driver element of the projectile, and/or repulsing the projectile on the proximal stop element.

18. The method according to claim 17, wherein the supply and/or discharge of the pressure medium is carried out continuously.

* * * * *